United States Patent
Martínez et al.

(10) Patent No.: US 12,269,871 B2
(45) Date of Patent: Apr. 8, 2025

(54) GENERATION OF A NEW SITE-SPECIFIC MONOCLONAL ANTIBODY FOR TAU PROTEIN AND ITS USE AS A TOOL IN SPECIFIC BIOMARKERS FOR EARLY DETECTION OF NEURODEGENERATIVE DISEASES AND PATHOLOGIES

(71) Applicant: CORPORACIÓN CENTRO INTERNACIONAL DE BIOMEDICINA ICC, Santiago (CL)

(72) Inventors: Leonardo Guzmán Martínez, Santiago (CL); Camila Calfio Painemal, Santiago (CL); Andrea González Zuñiga, Santiago (CL); Ricardo Maccioni Baraona, Santiago (CL); Constanza Maccioni Romero, Santiago (CL)

(73) Assignee: CORPORACIÓN CENTRO INTERNACIONAL DE BIOMEDICINA ICC, Santiago (CL)

( * ) Notice: Subject to any disclaimer, the term of this patent is extended or adjusted under 35 U.S.C. 154(b) by 182 days.

(21) Appl. No.: 17/825,511

(22) Filed: May 26, 2022

(65) Prior Publication Data

US 2022/0389087 A1    Dec. 8, 2022

(51) Int. Cl.
   *C07K 16/18*    (2006.01)
   *A61K 39/00*    (2006.01)
   *G01N 33/68*    (2006.01)

(52) U.S. Cl.
   CPC ......... *C07K 16/18* (2013.01); *G01N 33/6896* (2013.01); *A61K 2039/505* (2013.01); *C07K 2317/34* (2013.01); *C07K 2317/565* (2013.01); *G01N 2800/2821* (2013.01)

(58) Field of Classification Search
   None
   See application file for complete search history.

(56) References Cited

U.S. PATENT DOCUMENTS

| | | | |
|---|---|---|---|
| 9,012,237 B2 | 4/2015 | Maccioni et al. | |
| 2010/0124756 A1 | 5/2010 | Ray et al. | |
| 2010/0159486 A1 | 6/2010 | Liotta et al. | |
| 2012/0087861 A1 | 4/2012 | Nitsch et al. | |
| 2012/0122703 A1 | 5/2012 | Williams et al. | |

(Continued)

FOREIGN PATENT DOCUMENTS

WO    2015004163    1/2015

OTHER PUBLICATIONS

González et al. Plasma Tau Variants Detected by a Novel Anti-Tau Monoclonal Antibody: A Potential Biomarker for Alzheimer's Disease. Journal of Alzheimer's Disease, vol. 77, No. 2, pp. 877-883 (Year: 2020).*

(Continued)

*Primary Examiner* — Daniel E Kolker
*Assistant Examiner* — Hilary Ann Petrash
(74) *Attorney, Agent, or Firm* — Leonid Kisselev

(57) ABSTRACT

The present invention refers to a new site-specific monoclonal antibody for tau protein and its use as a tool in specific biomarkers. It also discloses the process of generating said site-specific monoclonal antibody, and kits for early detection of neurodegenerative diseases and pathologies involved with the tau protein, such as Alzheimer's and other types of dementia.

5 Claims, 6 Drawing Sheets

Specification includes a Sequence Listing.

(56) References Cited

U.S. PATENT DOCUMENTS

| | | |
|---|---|---|
| 2012/0276009 A1 | 11/2012 | Pfeifer et al. |
| 2014/0086921 A1 | 3/2014 | Griswold-Penner et al. |
| 2015/0050215 A1 | 2/2015 | Novak et al. |
| 2015/0183855 A1 | 7/2015 | Diamond et al. |
| 2015/0344553 A1 | 12/2015 | Weinreb et al. |
| 2016/0102138 A1 | 4/2016 | Iqbal et al. |
| 2016/0347804 A1 | 12/2016 | Griswold-Penner et al. |
| 2017/0015738 A1 | 1/2017 | Pedersen et al. |
| 2017/0058024 A1 | 3/2017 | West et al. |

OTHER PUBLICATIONS

Arigo Biolaboratories. MSDS Sheet. (Human Tau ELISA kit ARG81145, MSDS last updated Jul. 20, 2016) (Year: 2016).*

Motion Medical Distributing (#1601-2 Blood Draw Kit, Aug. 9, 2019) (Year: 2019).*

Google date search: Motion Medical Distributing (#1601-2 Blood Draw Kit, Aug. 9, 2019) (Year: 2019).*

Milstein, C. (1982), Monoclonal Antibodies. Cancer, 49: 1953-1957. Available at: https://doi.org/10.1002/1097-0142 (May 15, 1982)49:10<1953::AID-CNCR2820491002>3.0.CO;2-H, (accessed May 31, 2022).

Guzmán-Martínez, Leonardo, et al. "The Alz-tau biomarker for Alzheimer's disease: Study in a Caucasian population." Journal of Alzheimer's Disease 67.4 (2019): 1181-1186.

Sengupta, Urmi, et al. "Tau oligomers in cerebrospinal fluid in Alzheimer's disease." Annals of clinical and translational neurology 4.4 (2017): 226-235.

Blennow, Kaj, and Henrik Zetterberg. "Biomarkers for Alzheimer's disease: current status and prospects for the future." Journal of internal medicine 284.6 (2018): 643-663.

Chhatwal, J. P., et al. Plasma N-terminal tau fragment levels predict future cognitive decline and neurodegeneration in healthy elderly individuals. Nat Commun. 2020; 11 (1): 6024.

* cited by examiner

Healthy subjects / Alzheimer's Disease

Fig. 3.

Multiple sequence alignment

```
ASP-NTauDigest-AbTau S1             ----------------------------------DQGGYTMHQD------AGLKESPLQTPTEDXXSTPT  30
ChymotrypsinTauDigest-AbTau S1      MAEPRQEFEVMEDHAGTYGLGDRKDQGGY----------------------------------------  29
trypsinTauDigest-AbTau S1           ------QEFEVMEDHAGTYGLGDRKDQGGYTMHQDQEGDTDAGLKESPLQTPTEDGSEEPGS         55
                                                                      *****

ASP-NTauDigest-AbTau S1             AE--------------------------------  32
ChymotrypsinTauDigest-AbTau S1      ----------------------------------  29
trypsinTauDigest-AbTau S1           SETSDAKSTPTAEDVTAPLVDEGAPGK         82
```

Fig. 4.

Multiple sequence alignment

```
TauS EpitopeBovineTau    pgtpgsrsrtpslptpptrepkkvavvrtppk   32
TauS1Epitope             ---dqggy------------------------    5
                            *
```

ND OF A NEW SITE-SPECIFIC
MONOCLONAL ANTIBODY FOR TAU
PROTEIN AND ITS USE AS A TOOL IN
SPECIFIC BIOMARKERS FOR EARLY
DETECTION OF NEURODEGENERATIVE
DISEASES AND PATHOLOGIES

This present application incorporates by reference the material submitted in ASCII text file named SequenceListingTau, created on May 26, 2022, and having a size of 6.41 kilobytes.

FIELD

The present invention relates to specific biomarkers and kits for early detection and diagnosis of neurodegenerative diseases and pathologies associated with tau protein, such as Alzheimer's disease and other types of dementia.

BACKGROUND

Alzheimer's Disease (AD) is a multifactorial pathology that involves a difficult treatment, requiring early diagnosis for controlling or reducing its effects. AD has a great impact on the public healthcare system and is the most common type of dementia, raking the seventh cause of death worldwide after cardiovascular disorders. AD involves high social and economic costs, only being surpassed by ischemic cardiopathy and cancer. AD prevalence worldwide is 12% among people over 65 years of age, where the mortality rate amounts to about 2.4 million people a year, and the cost for world economy amounts, each year, to USD 600 billion.

One of the main inconveniencies of AD is that, currently, there are no effective biomarkers that can help diagnose this disease at the preclinical and clinical stages. Potential AD biomarkers have been disclosed, but these candidates are costly and/or highly invasive. For instance, markers for the disease have been proposed in the state of the art, such as: magnetic resonance imaging (MRI), positron emission tomography (PET) and those requiring the collection of cerebrospinal fluid (CSF) by way of lumbar puncture. Although they have made considerable progress in showing how these biomarkers are related to AD pathophysiology, their high cost and degree of invasiveness prevent their routine use for patient follow-up as well as for searching new drugs. In this context, a growing set of potentially less invasive blood cell-based biomarkers have been reported to support pre-clinical diagnosis of AD as well as to predict progression of the disease.

For example, U.S. Pat. No. 9,012,237 B2 discloses a method for non-invasive diagnose of AD by using previously known antibodies that recognize different tau variants. The method is based on using blood samples, specifically platelets (E4), to detect tau variants.

Document US 2010/0124756 describes a method for non-invasive diagnose of AD comprising detection and quantification of 16 blood markers. The document includes on an extensive list of alternative markers, where P199 tau marker is mentioned.

Patent application US 2010/0159486 discloses low molecular weight (LMW) peptides that are indicative of neurological conditions, such as AD, cognitive impairment and brain microhemmorhages. The biomarker corresponds to a peptide associated with a metabolic pathway or cellular process, such as inflammation, estrogen activity, among others. Evaluation of patient samples for the presence of such LMW peptides is an effective means of detecting neurological conditions and monitoring disease progression. LMW peptides are particularly useful for detecting neurological conditions during the early stages without invasive procedures.

Invention patent application US 2012/0122703 relates to the identification of variants in the CLU/APOJ, PICALM, ABCA7, CR1 or BIN1 gene loci or the MS4A gene cluster which are novel risk indicators for the development of AD. The essayed DNA was obtained from blood samples US 2012/0087861 discloses human tau-specific antibodies that recognize tau protein, including pathologically phosphorylated tau and aggregated forms of tau. The purpose of the invention comprises the use of samples such as blood, CSF, urine, plasma, B cells, cell cultures, tissue biopsy, neural tissue.

Patent application US 2012/0276009 discloses anti-phosphorylated tau monoclonal antibodies for diagnose of pathologies associated with tau. These antibodies can be used in fluid samples such as blood, plasma, urine, CSF and serum.

US 2014/0086921 relates to a therapeutic treatment for reducing A-beta peptide ($\alpha\beta$) by administering a monoclonal anti-tau antibody. The antibodies used are also proposed as a method of monitoring tau concentration and possible extracellular tau (etau) in samples, for example, in CSF, blood, plasma, serum, urine and saliva.

Invention patent application US 2015/0050215 provides therapeutic and diagnostic antibodies, as well as their fragments, portions, derivatives and variants thereof, that bind to regions of the tau protein. The invention also relates to methods of using those antibodies for diagnostics, prevention, and treatment of Alzheimer's disease and related tauopathies. Also disclosed is the injection of antibodies and/or peptide vaccines that elicits an immune response directed at pathological tau proteins and tau deposits in the brains of patients. Suitable vaccines represent a tau peptide carrying one or more of the tau therapeutic epitopes.

US 2015/0183855 proposes antibodies to tau having therapeutic properties. The antibodies design have the function of binding etau from body fluids, and preventing tau aggregates from entering adjacent cells. Tau, in this document, may be detected in blood, plasma, serum, urine, CSF, and interstitial fluid samples.

Application US 2015/0344553 provides new tau-specific human antibodies, as well as fragments, derivatives and variants of said antibodies. Assays, kits, and solid supports related to tau-specific antibodies are also disclosed. Further, the antibody, immunoglobulin chains, as well as binding fragments, derivatives and variants thereof, can be used in pharmaceutical and diagnostic compositions for tau targeted immunotherapy and diagnosis.

Patent application US 2016/0102138 discloses a method of treating tau pathologies, such as Alzheimer's disease, involving the administration of antibodies specific to the amino terminal region of human tau (amino acid residues 6-18 or 184-195) to provide passive immunization. Administration of such antibodies can reduce total tau levels, decrease tau hyperphosphorylation, and improve reference memory.

US 2016/0347804, discloses isolated tau peptides and compositions comprising said peptides. Further provided are antibodies specific for an isolated tau peptide, and methods of using the isolated tau peptide in diagnostic and treatment, including the use of a pharmaceutical composition comprising isolated tau peptide for stimulating an immune response in an individual to a tau peptide, and methods of using antibodies in the detection, diagnosis, and treatment of disorders.

Invention US 2017/0015738 relates to a novel class of monoclonal antibody that specifically binds the phosphorylated serine 396 residue on pathological hyperphosphorylated (PHF) tau (pS396), as well as to methods of using these molecules and their tau binding fragments in the treatment of Alzheimer's disease and tauopathies.

US 2017/0058024 provides an isolated antibody or antigen-binding fragment that specifically binds tau, the antibody or fragment comprising a heavy chain variable (VH) region and a light chain variable (VL) region. Methods to prevent or treat a tauopathy in a subject are also provided, including the administration of therapy to a human in need with one or more antibodies or fragments thereof.

Invention patent application WO2015/004163 provides for tau antibodies, antibody with improved binding capacity for tau antigen. In particular, the invention provides improved compositions, methods and kits comprising such antibodies or fragments thereof.

Due to the latter, it is necessary to develop a reliable molecular marker that is related to clinics, for early detection of AD that involves patient diagnosis and follow-up, as well as a quantitative parameter in the evaluation of possible new drugs for controlling AD. A unique discovery has been finding a tau protein in different cells of the nervous system, such as platelets.

A list of blood biomarkers has been published, but none has been clinically validated for Alzheimer's disease. Due to this, the tau protein has become the target for a successful new AD biomarker.

Thus, the present invention provides specific biomarkers and kits for early detection and diagnosis of neurodegenerative diseases and pathologies associated with tau protein, such as Alzheimer's disease and other types of dementia, where said biomarker corresponds to an anti-tau antibody having greater sensitivity and specificity than the commercially available tau5 antibody, having a greater immunoreactivity in high molecular-weight tau protein variants in subjects with the disease as compared to cognitively healthy subjects.

SUMMARY

The present invention refers to a new site-specific monoclonal antibody for tau protein and its use as a tool in specific biomarkers. It also discloses the process for generation of said site-specific monoclonal antibody, and kits for early detection of neurodegenerative diseases and pathologies associated with the tau protein, such as Alzheimer's and other types of dementia.

BRIEF DESCRIPTIONS OF DRAWINGS

FIG. 3 shows a multiple sequence alignment as obtained by enzymatic digestion, where said sequences are recognized by the monoclonal antibody tau51 of the present invention.

FIG. 4 shows a multiple sequence alignment, in which the epitope disclosed for the commercially available tau5 antibody is compared to the new monoclonal antibody tau51 of the present invention.

DETAILED DESCRIPTION

The present invention discloses an innovative site-specific monoclonal antibody for tau protein and its application for biomarkers and kits for early detection and diagnosis of neurodegenerative diseases and pathologies associated with tau protein such as Alzheimer's Disease and other types of dementia, where said biomarker corresponds to an anti-tau antibody having greater sensitivity and specificity than the commercially available tau5 antibody, having greater immunoreactivity in high molecular weight tau protein variants in subjects having the disease, as compared to cognitively healthy subjects.

Figure 1A:
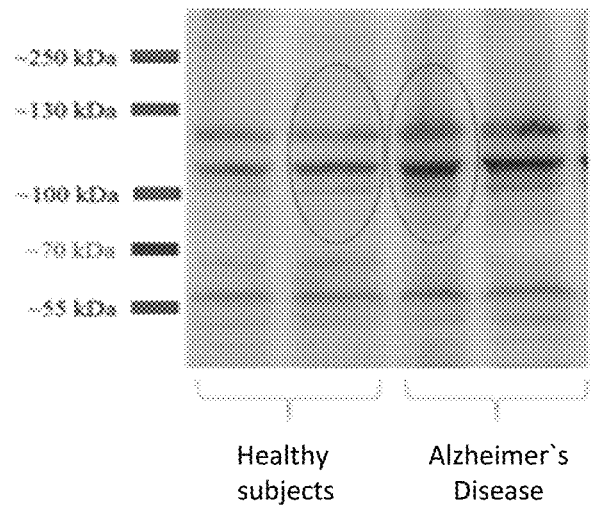
FIGS. 1A-1C show representative Western blot assay of platelet tau with the monoclonal antibody tau51 of the present invention.
Figure 1B:
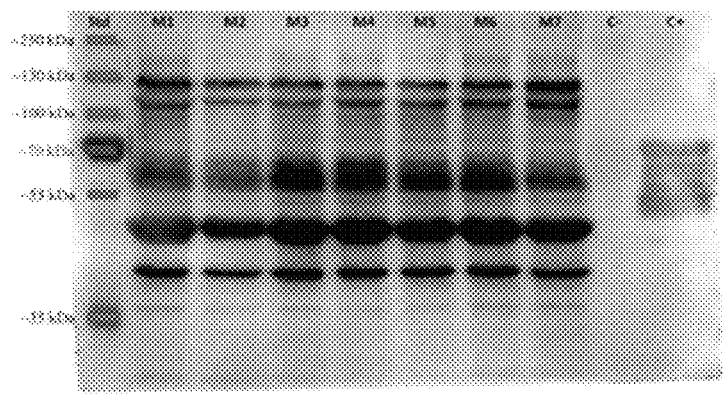
Figure 1C:
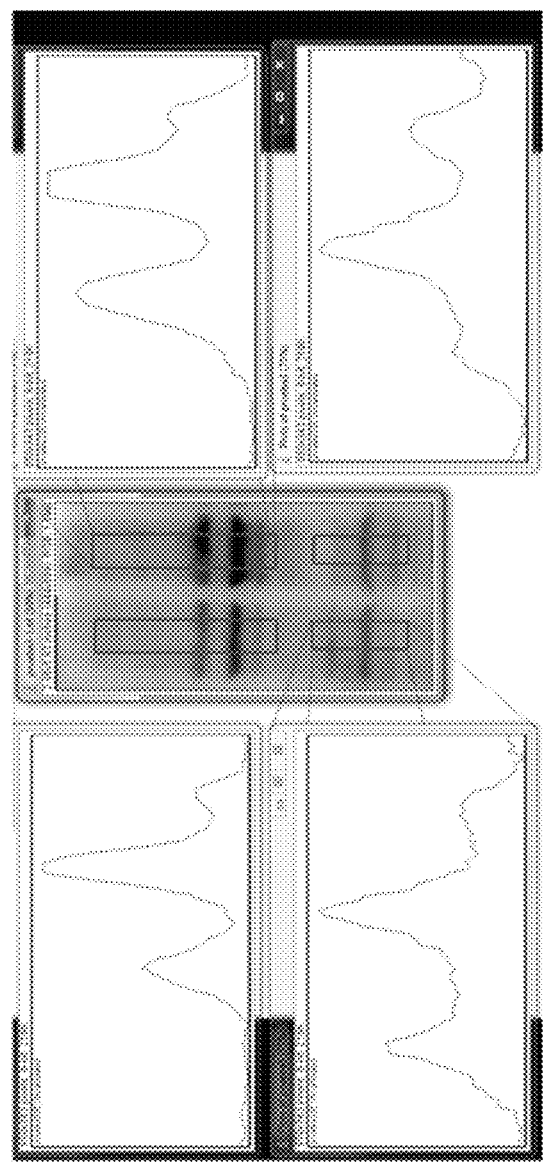

FIGS. 1A-1C show representative Western blot assay of platelet tau with the monoclonal antibody tau51 of the present invention. FIG. 1A shows the results of the Western blot assay for monoclonal antibody tau51, wherein the expression of the tau51 protein variants in healthy patients and those diagnosed with Alzheimer's was compared. FIG. 1B shows the recognition profile of the tau-protein variants in different platelet protein samples with the tau51 antibody. A representative scheme of the determination of tau protein variants is shown in FIG. 1C. These Western blots of platelet proteins show that tau51 antibody recognizes the tau protein variants, the low molecular weight variant (LMWtau), and the high molecular weight variant (HMWtau).

Figure 2:
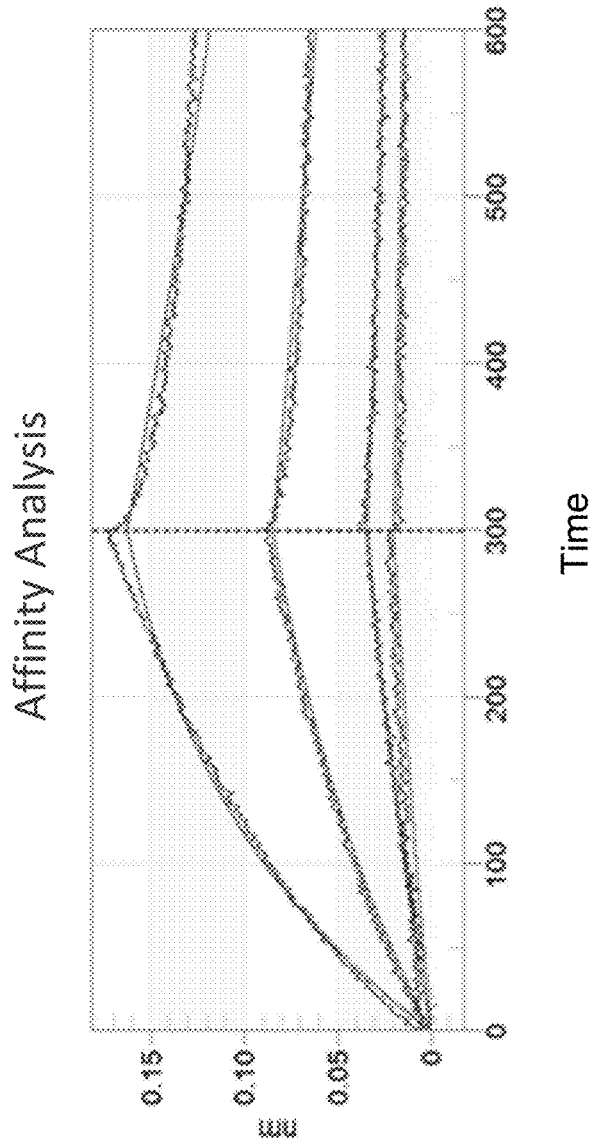
FIG. 2 shows an OCTET affinity assay of monoclonal antibody tau51 with purified recombinant human tau protein.

FIG. 2 shows an OCTET affinity assay of monoclonal antibody tau51 with purified recombinant human tau protein.

FIG. 3 shows a multiple sequence alignment as obtained by enzymatic digestion, where said sequences are recognized by the monoclonal antibody tau51 of the present invention.

FIG. 4 shows a multiple sequence alignment, in which the epitope disclosed for the commercially available tau5 antibody is compared to the new monoclonal antibody tau51 of the present invention.

Figure 5:
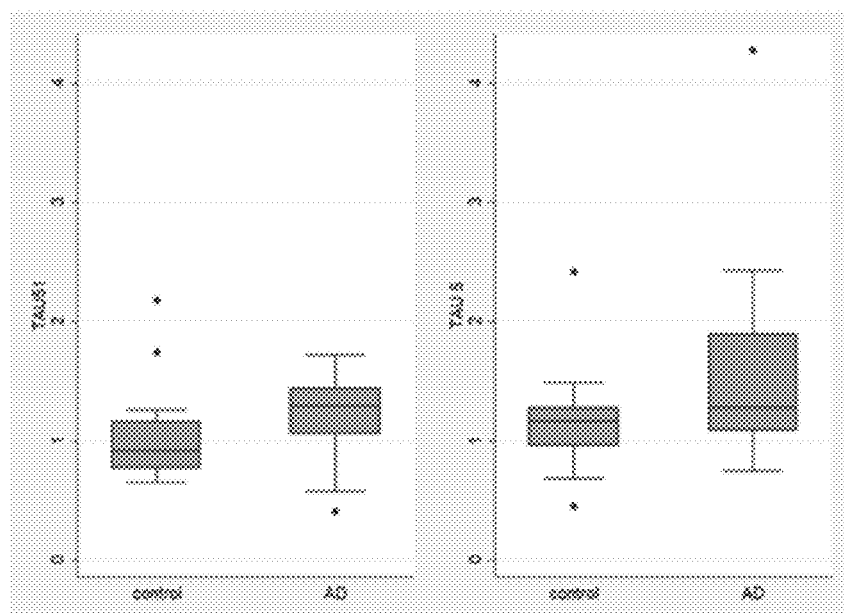
FIG. 5 shows an immunoreactivity assay, comparing the monoclonal antibody tau51 of the present invention to the commercially available tau5 antibody. The graphs are represented in arbitrary units of densitometric quantitation of tau protein species.

FIG. 5 shows an immunoreactivity assay, comparing the monoclonal antibody tau51 of the present invention to the commercially available tau5 antibody. The graphs are represented in arbitrary units of densitometric analysis of tau protein variants.

Figure 6A:
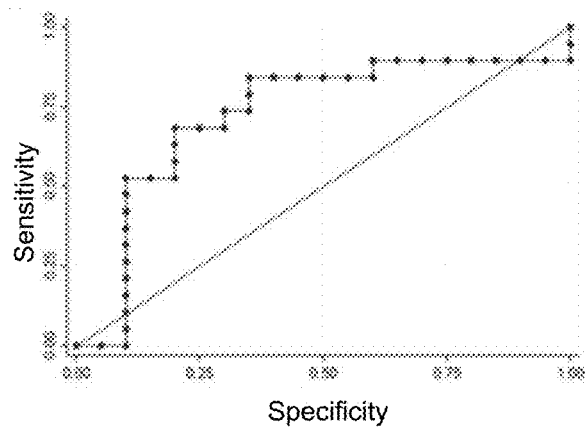
FIGS. 6A-6B show the sensitivity and specificity of the algorithm for platelet tau as a biomarker to detect Alzheimer's disease through ROC curve assays.
Figure 6B:
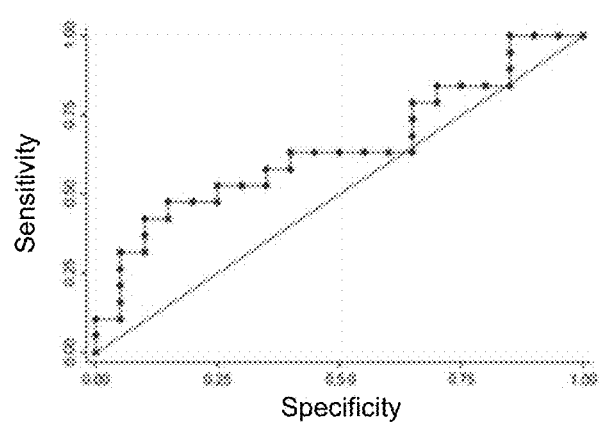

FIGS. 6A-6B show the sensitivity and specificity of the algorithm for platelet tau as a biomarker to detect Alzheimer's disease through ROC curve assays. FIG. 6A shows an area below the 0.73 curve; 68.42% sensitivity, and 75% specificity (optimal for a biomarker). Observed in FIG. 6B can be an area below the 0.64 curve; 63.16 sensitivity, and 62% specificity, respectively.

Figure 7A:
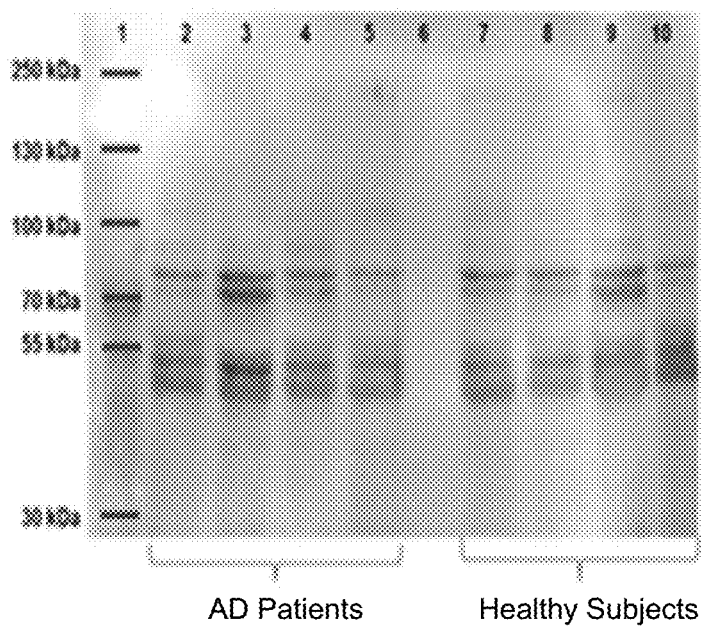
FIGS. 7A-7B show that the monoclonal antibody tau51 recognizes tau in plasma.
Figure 7B:
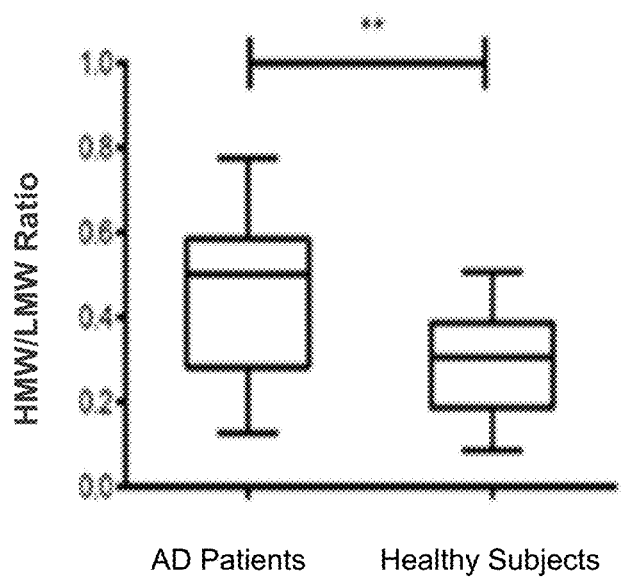

FIGS. 7A-7B show that the monoclonal antibody tau51 recognizes tau in plasma. FIG. 7A shows the results of a representative Western blot assay on plasma samples from patients having Alzheimer's Disease and control subjects. FIG. 7B shows the high molecular weight (HMW) and low molecular weight (LMW) variant ratio, as evaluated by densitometry, of plasma samples from Alzheimer's Disease patients and control subjects.

One of the embodiments of the present invention discloses an antibody used as a biomarker for early detection of neurodegenerative diseases and tau-protein associated pathologies, such as Alzheimer's disease and other types of dementia, including a monoclonal antibody tau51, comprising:
- a light chain variable (VL) region having a sequence with at least 85 percent sequence identity of SEQ ID NO: 2 comprising:
  - an amino acid sequence of LCDR1 with at least 85 percent sequence identity of SEQ ID NO: 4;
  - an amino acid sequence of LCDR2 with at least 85 percent sequence identity of SEQ ID NO: 6, and
  - an amino acid sequence of LCDR3 with at least 85 percent sequence identity of (SEQ ID NO: 8; and
- a heavy chain variable (VH) region having a sequence with at least 85 percent sequence identity of SEQ ID NO: 10 comprising:
  - an amino acid sequence of HCDR1 with at least 85 percent sequence identity SEQ ID NO: 12,
  - an amino acid sequence of HCDR2 with at least 85 percent sequence identity of SEQ ID NO: 14, and
  - an amino acid sequence of HCDR3 with at least 85 percent sequence identity of SEQ ID NO: 16.

In one of the embodiments of the present invention, the sequence identities of the amino acid sequences are between 85 to 100%, according to the list of sequences in the present invention. The codons of a recombinant nucleic acid molecule encoding proteins as herein disclosed can be replaced by synonymous codons (known, in the state of the art, as silent substitution).

In one of the embodiments of the present invention, said antibody allows the detection of high and low molecular weight tau-protein variants, (HMWtau) and (LMWtau).

In one of the embodiments of the present invention, said antibody is associated with a molecular marker to be detected via Western Blot, radioimmunoassay, enzyme immunoassay, fluoroimmunoassay, immunochemiluminescence assay, flow cytometry techniques, or combinations thereof.

One of the embodiments of the present invention discloses a biomarker kit for early detection and diagnosis of neurodegenerative diseases and tau protein-associated pathologies such as Alzheimer's and other types of dementia, where said kit comprises:
i) Reagents for extracting blood samples from an individual;
ii) Chemical reagents for extracting blood proteins, platelet proteins and blood plasma proteins before analyzing the samples;
iii) Chemical reagents for determining the concentration of proteins present in the samples;
iv) Chemical reagents for performing immunoassays, including a monoclonal antibody tau51; and
v) Instructions for performing a test according to the method and interpreting the results.

Disclosed in one of the embodiments of the present invention is the use of a biomarker antibody for preparation of a useful formulation for early detection and diagnosis of neurodegenerative diseases and tau protein-associated pathologies, preferably Alzheimer's disease. Early detection and diagnosis of neurodegenerative diseases and tau protein-associated pathologies is carried out in samples of blood, platelets and/or blood plasma.

In one of the embodiments of the present invention, the biomarker antibody is used for immunotherapy of neurodegenerative diseases and tau protein-associated pathologies, preferably Alzheimer's disease.

In one of the embodiments of the present invention, the biomarker antibody is used for preparation of a medical device useful for early detection and diagnosis of neurodegenerative diseases and tau protein-associated pathologies, preferably Alzheimer's disease, where early detection of neurodegenerative diseases and tau protein-associated pathologies is carried out in samples of blood, platelets and/or blood plasma.

In one embodiment of the present invention, a pharmaceutical composition comprising the monoclonal antibody tau51 according to the present invention and a pharmaceutically acceptable carrier are disclosed.

Disclosed in one of the embodiments of the present invention is the use of a biomarker kit for preparation of a useful formulation for early detection and diagnosis of neurodegenerative diseases and tau protein-associated pathologies, preferably Alzheimer's disease, where early detection and diagnosis of neurodegenerative diseases and tau protein-associated pathologies is carried out in samples of blood, platelets and/or blood plasma.

Disclosed in one of the embodiments of the present invention is a method for early detection and diagnosis of neurodegenerative diseases and tau protein-associated pathologies, such as Alzheimer's and other types of dementia, said method comprising the steps of:
a) characterizing quantities of high and low molecular weight tau protein variants in a reference population of persons that do not suffer from neurodegenerative diseases and pathologies involved with tau protein, such as Alzheimer's and other types of dementia;
b) extracting blood samples from an individual;
c) extracting blood proteins, platelet proteins and blood plasma proteins from the blood samples of an individual;
d) determining the concentration of proteins present in the samples;
e) Analyzing the protein extracts obtained from step d) through immunoassays with the monoclonal antibody tau51;
f) comparing the relative amounts of high and low molecular weight tau protein variants in the blood, plasma and platelets of said patient to those of said reference population and determining the degree of oligomerization of the neurodegenerative disease-associated tau protein and tau protein-associated pathologies, such as Alzheimer's and other types of dementia, wherein said oligomerization refers to the quotient between the high molecular weight of the tau protein variant;

In one of the embodiments of the present invention, the variants of low molecular weight tau protein (LMWtau) are those with a molecular weight less than 70 kDa and variants of the high molecular weight tau protein (HMWtau) are those having a molecular weight higher than 70 kDa. The HMWtau/LMWtau algorithm correlates with the degree of cognitive impairment in AD patients, reason by which it is an appropriate marker for disease detection and diagnosis.

In one of the embodiments of the present invention, the immunoassay of step e) can be selected from Western Blot assay, radioimmunoassay, enzyme immunoassay, fluoroimmunoassay, immunochemiluminescent assay, flow cytometry, or combinations thereof.

Disclosed in one of the embodiments of the present invention is a process to generate a platelet protein antigen to be recognized by the monoclonal antibody tau51, for early detection and diagnosis of neurodegenerative diseases and tau protein-associated pathologies, such as Alzheimer's disease and other types of dementia, wherein said process comprises the steps of:
 a) obtaining venous blood samples;
 b) extracting platelet proteins from the samples collected in a);
 c) removing white cells and red blood cells remaining in the sample;
 d) resuspending the platelet pellet in ammonium chloride and wash with neutral pH buffer solutions;
 e) performing platelet lysis using RIPA lysis buffer and protease inhibitors;
 f) reacting the platelet lysate with a monoclonal anti-tau antibody, in a binding buffer solution;
 g) mixing a magnetic bead suspension with a sample of platelet tau protein and incubating this solution;
 h) collecting the beads from the solution obtained in g) using a magnetic support and washing with a wash buffer;
 i) performing one or more than one denaturing elution using a reducing sample loading buffer to obtain a platelet protein antigen to be recognized by the monoclonal antibody tau51.

Disclosed in one of the embodiments of the present invention is a process to generate the monoclonal antibody tau51 according to monoclonal production technology [Milstein C. (1982), Monoclonal antibodies. *Cancer* 49, 1953-1957.], for early detection and diagnosis of neurodegenerative diseases and tau protein-associated pathologies, such as Alzheimer's and other dementias. Said process comprises the steps of injecting highly purified platelet tau protein into Balb/c mice (0.2 mg/mouse). Following primary injection and a boost, B cells are fused with myeloma cells, in a cell culture medium, collecting the resulting pellet, and seeding in cell culture dishes. Culturing in selection media is followed by the steps of screening and subcloning the viable antibody-producing hybridomas. Subsequently, the hybridomas were cultivated in a cell culture medium and characterized. Finally, the last stage comprises the steps of purifying and storing the antibodies obtained.

EXAMPLES

In light of the above, those skilled in the art will understand that changes can be made to the specific aspects disclosed, and, still, being able to obtain the same or similar result without departing from the spirit and scope of the invention. Therefore, the specific functional and structural details herein disclosed are must not be construed as limiting. It should be understood that the entire disclosure of each reference herein cited is incorporated within the disclosure of the present application.

Example 1: Patient Selection for Clinical Studies

To determine the validity of the new detection kit antibody, a population of cognitively healthy control subjects was compared to a population of subjects having AD within the same age range, and thus to verify that the diagnostic kit allows to discriminate one group from the other.

The protocol for assays with Alz-Tau® was approved by the ethics committee of the Eastern Metropolitan Health Service (SSMO) and the subjects signed the informed consent approved by the same entity to participate in the study.

After the clinical evaluation was carried out, a venous blood samples were taken, which were transferred and subsequently processed at the Laboratory of Neuroscience and Functional Medicine laboratory of the International Center for Biomedicine ICC. Each blood sample was comparatively analyzed with the commercially available monoclonal tau5 antibody, and with the monoclonal antibody tau51 that is disclosed in the present invention.

Concurrently to the blood-sample collection, the subjects underwent a neuropsychological interview comprising several tests, the result of each test being compared to the result of the biomarker for each subject, so as to establish whether there is a predictive correlation between both. After obtaining all the information, the respective statistical analysis was performed. All the subjects were evaluated by trained clinicians, unaware of the results of the neuropsychological evaluation and blood markers. The blind test was opened after obtaining information from all subjects with a formal authorization from the sponsor to proceed with the statistical analysis of the results.

Recruited for the study were 39 subjects that completed the study, 20 controls (C) and 19 subjects having mild to moderate Alzheimer's disease (AD). In order for them to be eligible for the study, the diagnosis of each subject was confirmed by a clinical evaluation consisting of a structured interview, and including:
 i) Detailed medical history;
 ii) CDR, administered by a clinician trained to classify the subject as normal control or with dementia; in turn, to determine the level of severity in subjects diagnosed with dementia.
 iii) family history of dementia;
 iv) medical events (cardiovascular risk factors);
 v) current treatment and comprehensive neurological examination.

Once the informed consent form process, as previously approved by the SSMO ethics committee, has been completed, fulfillment of the below listed criteria will be verified, namely:

Patients with AD
Inclusion Criteria:
 (i) Diagnosis of probable AD according to NINCDS-ADRDA criteria;
 (ii) Clinical Dementia Rating (CDR)≥1;
 (iii) Brain scan performed in the past months to exclude patients with focal lesions such as brain tumors, subdural hematomas, strokes, and central nervous system infections, which must be provided by him/her or his/her caregiver;
 (iv) at least 4 years of education;
 (v) Presence of an informant who could provide adequate information for the evaluation, and
 (vi) Accept the study protocol through the informed consent signed by patient.

Exclusion Criteria:
 (i) significant leukoaraiosis (>25% of total white matter area) [19];
 (ii) history of cerebrovascular accidents or silent infarcts being 2 cm in diameter o over, located in strategic regions;
 (iii) severe cognitive impairment that could interfere with the neuropsychological assessment;

(iv) significant presence of depressive symptoms documented by the Structured Clinical Interview for DSM IV criteria for Depression;
(v) significant underlying mental or psychiatric illnesses that may affect cognition;
(vi) sensory disturbances that could interfere with the neuropsychological assessment. Subjects between 60 to 90 years of age.

Healthy Person Controls:
Inclusion Criteria:
(i) No cognitive impairment in accordance with medical history;
(ii) at least 4 years of education;
(iii) over 24 points in Folstein's Minimental State Examination (MMSE);
(iv) presence of an informant who could provide information for the assessment; and
(v) willingness to participate after informed consent in the study procedures. Subjects between 60 to 90 years of age.

Neuropsychological Tests.

The neuropsychological evaluation was independently administered by trained neuropsychologists of our work team, blinded to the clinical evaluation. The recruited subjects were given a set of adequate neuropsychological tests to determine the degree of cognitive impairment and cognitive abilities commonly affected by AD, that is:
I. Folstein's Minimental State Examination (MMSE);
II. Global cognitive functions with: Addenbrooke's Cognitive Examination Revised (ACE-R);
III. Memory Impairment Screen (MIS);
IV. Test language (Boston Naming Test);
V. Verbal fluency (FAS) and semantic fluency tasks (animals in minute);
V. Visuospatial-constructive function (Rey 1941).
VII. Working memory test (Digit Hold).
VII. Verbal episodic memory test (Free and Cued Selective Reminding Test, FCSRT or Free and Cued Selective Reminding Test with immediate recall).
IX. To measure the executive function, the following were used: a Frontal Assessment Battery (FAB) [25]. Trail Making Test A and B;
X. Activities of daily living are examined with: Activities of Daily Living Questionnaire (T-ADLQ), during an interview with a companion (caregiver or family member);
XI. Mood is evaluated with: Cornell Depression Test;
XII. Goldberg Health Questionnaire;
XIII. Global appreciation is established with: Reisberg Global Deterioration Scale;
XIV. Abbreviated Barcelona Test.

Example 2: Sample Taking and Processing

Extraction of Blood Samples:

With the patient sitting in a chair with his/her arm on the armrest, 6 mL of peripheral venous blood was extracted from the antecubital veins using a K2EDTA vacutainer system for biomarker protein analysis. Blood samples were kept and transported at room temperature to the laboratory in order to carry out the steps of protein extraction and western blot. The samples were kept in K2E vacutainer tubes with 10.8 mg EDTA, and the blood was processed within 2 hours following collection thereof.

Sample Processing:

For processing samples, the protocols detailed below were strictly followed:

Platelet Protein Extraction:

6 mL of venous blood were centrifuged by differential centrifugation at 250 RCF (Relative Centrifuge Force) for 10 minutes at room temperature. Thus, the platelet-rich plasma (PRP) supernatant, as carefully removed from these tubes, was poured into 1.5 mL centrifuge tubes. Next, a second centrifugation of PRP was performed at 250 RCF to eliminate white cells and red blood cells remaining in the sample. The plasma obtained from this second centrifugation was subjected to a new centrifugation at 1750 RCF for 10 minutes at room temperature in order to isolate the platelets from the rest of the plasma components.

Then, the platelet pellet was resuspended at 0.83% NH4Cl and kept on ice for 5 minutes. The platelet suspension was again centrifuged at 1750 RCF for 10 minutes at a temperature of 4° C. The platelet pellet was subjected to two wash steps, taking care not to disintegrate the pellet, using 100 mM EGTA in 1× PBS, or phosphate buffered saline (1.4 mM NaCl, 0.02 mM KCl, 0.1 mM Na2HPO4, 0.017 mM KH2PO4), 100 mM EGTA).

Platelets were lysed using 100 μL of RIPA lysis buffer (5.0 mM Tris-HCl pH 7.5; 1.5 mM NaCl; 10% NP-40; 10% deoxycholate; 20 mM EDTA pH 8.0; 500 mM NaF; 1% SDS) supplemented with a protease inhibitor cocktail (Roche). After the platelet lysis process, a final centrifugation was carried out using 1600RCF for 10 minutes at 4° C.

Obtaining Platelet Protein Antigens to be Recognized by the Monoclonal Antibody Tau51:

Proteins were extracted from the platelet samples obtained in the previous steps. To this effect, in each reaction, 100 μg of platelet lysate were combined with 20 μg of monoclonal tau5 antibody in a total volume of 600 μL with binding buffer. PBS with 0.01% Tween® 20 was used as binding/wash buffer. The reaction was incubated at room temperature for 2 hours with shaking.

200 μL of PureProteome™ Magnetic Bead Suspension (Millipore, cat#LSKMAGG10) was added to a 1.5 mL microcentrifuge tube. Using the neodynium magnetic support, the beads were washed with 500 μL of binding buffer by vigorous vortexing for 10 seconds, picking up the beads on the magnet and removing the buffer with a pipette.

400 μL of the tau5 platelet tau sample was added to the beads and the mixture was incubated at room temperature for 30 minutes, with shaking. The unbound fraction was discarded and, as described above, the beads were washed three times with 500 μL wash buffer using the magnetic support to capture the beads.

Denaturing elution was performed by adding 100 μl of reducing 1× SDS-PAGE (sodium dodecyl sulfate polyacrylamide gel electrophoresis) sample loading buffer to the beads and incubating at 70° C. for 10 minutes. Further elution was performed in a similar manner with 50 μL to achieve maximum yield. Both elutions were collected using the magnetic support in the very microcentrifuge tube and were stored for subsequent analysis.

The isolated protein was quantified by nanodrop at 280 nm and stored at −20° C. until later use.

Collection of Monoclonal Tau51 Antibodies:

The process for generating the monoclonal antibody tau51 was performed according to monoclonal production technology [Milstein C. (1982), Monoclonal antibodies. Cancer 49, 1953-1957]. To this effect, highly purified platelet tau protein was injected into Balb/c mice (0.2 mg/mouse). Following the primary injection and a boost, B cells were fused with myeloma cells, in a RPMI medium with 10% FBS, the resulting pellet being harvested on cell culture plates. After culturing in selection media with hypoxanthine, aminopterin, and thymidine (HAT), the hybridomas were screened and subcloned to ensure that the viable antibody-producing hybridomas were available after the selection process. The hybridomas were cultured in RPMI 1640+L glutamine culture medium, supplemented with 10% FBS, 1× penicillin/streptomycin (100 IU/ml), and 1 mM sodium pyruvate. Finally, the antibodies were purified, using a Protein A column, quantified, and stored at −20° C.

Once the monoclonal antibodies of the present invention were obtained, they were sequenced using techniques known in the state of the art, via the service provided by The University of Texas MD Anderson Cancer Center.

To that effect, an RNA extraction through hybridoma 220B-51-1 (tau51) cells was performed. Total RNA was extracted from the clone of said hybridoma using the RNA extraction protocol (Zymo Research). Subsequently, an RT-PCR assay was performed, wherein cDNA was created from RNA by reverse transcription with random primers. After the above, PCR reactions using variable domain primers were performed to amplify the VH and VL regions of the DNA of the monoclonal antibody.

Subsequently, the VH and VL products were cloned into the Invitrogen sequencing vector pCR2.1-TOPO and DH5a cells were transformed with the vector, and later selected by PCR for positive transformants. The selected colonies were analyzed via DNA sequencing, according to the listing of sequences provided in the present invention.

Example 3: Western Blot Assay

For analyzing the protein extracts obtained, 50 µg of total platelet protein per well were applied to a 1 mm-thick 10% polyacrylamide gel. The electrophoretic run was performed at a constant 100V voltage for about 120 minutes. Once the electrophoretic run was completed, the proteins were analyzed by western blot. As for electroblotting, the proteins, still in the gels, were transferred to a nitrocellulose membrane with a pore size of 0.45 µm at 330 mA for 90 minutes. After the above, the membranes were blocked with 5% bovine serum albumin (BSA) for 1 hr at 25° C. (or overnight at 4° C.). Then, the membranes were incubated with the primary monoclonal antibody tau51, at a 2.5 µg/mL concentration in TBS1x/BSA 1%. Once the 0.01% Tween 20 was concluded over 30 minutes at 80 rpm, to eliminate the antibodies that did not bind to their antigen nor had an unspecific binding incubation with the primary antibody, the membranes were incubated with the secondary goat anti-mouse antibody at a 1:10,000 dilution, in accordance with the manufacturer's instructions. At the completion of each incubation stage with the antibodies, the membranes were washed with a TBS 1x solution, supplemented with 0.01% Tween 20, for 30 minutes at 80 rpm, to eliminate the antibodies that did not bind to their antigen or had unspecific binding.

Once the western blot stages (including development) were completed, using ImageJ 1.54j8 software of the National Institutes of Health (NIH), USA, the membranes were subjected to densitometric analysis of their bands with immunoreactivity to tau51. It was thus this way, it was thus possible to quantify low molecular weight (LMWtau) and high molecular weight (HMWtau) variants (oligomeric tau). The HMWtau/LMWtau algorithm correlates with the degree of cognitive impairment in AD patients, making it an appropriate marker for detection and diagnosis of the disease.

Thus, the relative intensities of the tau bands were quantified in the densitometric analyzes, and the HMWtau (>70 kDa) to LMWtau (<70 kDa) ratio and neuropsychology assessments were estimated. Finally, this allowed to quantify the progression of cognitive impairment due to Alzheimer's disease.

Statistical Analysis:

As for the statistical analysis of the results obtained in the examples above, the categorical variables were analyzed with frequency statistics. In turn, continuous numerical variables, such as Alz-Tau® algorithm for tau51 and tau5, age and raw scores on neuropsychological tests, were described through central trend statistics (mean and median) and dispersion statistics as standard deviation (SD) and interquartile range (IGR). On the other hand, a Shapiro-Wilk normality test was performed on the algorithm for tau51 and the algorithm for tau5, the normality hypothesis in cases where p-value <0.05 being dismissed.

A Fischer mean comparative test (t-test) was performed to determine whether there was a significant difference between the mean of the algorithm for tau51 in the Alzheimer Group and the mean in the Control Group. In turn, Pearson's (parametric) or Spearman's (non-parametric) correlation coefficients were calculated to describe whether there is an association between tau51 and neuropsychological test scores. A test was regarded as statistically significant when the p-value was below 0.10 with a confidence level of 90%. This is decided upon the low number of the sample. Finally, a logistic regression model was applied to determine whether the Alz-Tau® algorithm for tau51 is able to distinguish subjects with Alzheimer's disease from control subjects. To assess the model's fit, the area below the ROC curve (AUC) where AUC≥0.7 was acceptable, was used. This same analysis was performed on the tau5 algorithm.

Example 4: Studies with the Monoclonal Antibody Tau51

To verify the utility of the new tau51 antibody of the present invention, the procedure was detailed in examples 1, 2, and 3.

As for the western blot study, the immunoblots showed an electrophoretic pattern with immunoreactivity to tau51, similar to that of tau5, recognizing variants of the low molecular weight tau protein (LMWtau) below 70 kDa, and variants of the protein high molecular weight tau (HMWtau) over 70 kDa. HMWtau variants exhibited greater immunoreactivity in AD subjects with respect to subjects of the control group (FIG. 5).

On the other hand, the ROC curve analysis for the Alz-Tau® algorithm, both for tau51 and for tau5 (FIG. 6), showed, with the new monoclonal antibody tau51, 68.42% sensitivity, and 75% specificity, to discriminate between patients with AD and cognitively healthy subjects, with a cut-off point of 1,162 for the HMW/LMWtau ratio, and with an area under the curve of 0.73, exceeding the minimum level ≥0.7, a value allowing a biomarker to be considered appropriate (FIG. 6). In turn, positive and negative predictive values of 72.22% and 71.43%, respectively, were obtained, showing a diagnostic capacity of 71.79% of correctly classified cases, whereas the capacity with tau5 drops to 64.10%, with a positive predictive value of 72.73%, and a negative predictive value of 60.71%.

According to the statistical data obtained in the present invention, it was shown that the monoclonal antibody tau51 better discriminates between patients with AD as compared to control patients, with respect to the performance of the commercially available antibody tau5.

Example 5: Correlation Between Tau51 and Neuropsychological Test Scores

Since neuropsychological test scores do not present a normal distribution, a non-parametric correlation analysis was performed with Spearman's coefficient between tau51's Z score and Z score of each of the neuropsychological test scores. The asterisks indicate that the correlation is significant when p-value <0.05 (Table 1).

The results of the logistic regression show that, by each unit tau51 rises, the risk of being in the AD group increases by 81% (OR=1.81, p-value 0.10). This result, although it is not significant at a more demanding alpha level of 0.05 (5%), effectively is within the significance threshold of alpha=0.10.

TABLE 1

Tau51 correlation statistics with different cognitive tests.

| Cognitive tests | Spearman correlation between tau51 and test scores |
| --- | --- |
| TBA person's orientation | −0.3554* |
| TBA place orientation | −0.3639* |
| TBA direct digits | −0.3350* |
| TBA indirect digits | −0.4035* |
| BNT Boston Naming Test words | −0.3366* |
| King figure, copy category | 0.3392* |
| LAWTON by its name, IADL Scale | −0.3677* |
| MIS Memory Impairment Screen | −0.3509* |
| TBA person's orientation | −0.3489* |

Through statistical analysis, the present invention allows to determine that the monoclonal antibody tau51 has greater sensitivity, greater specificity, and less variability, as compared to the data obtained with the commercially available monoclonal antibody tau5.

As the present invention has been disclosed under the aforementioned embodiments, it might seem apparent that other alternatives, modifications or variations would yield the same results. However, we have been able to establish that the subject matter disclosed in the present application is essential for the success of the invention that is disclosed. Consequently, the embodiments of the invention are intended to be illustrative, not restrictive. Several changes may be made without departing from the spirit and scope of the invention as is defined in the claims below.

All the patents, patent applications, scientific papers and other public documents as known by applicant to constitute the state of the art, have been appropriately cited in the present application

What is claimed is:

1. A biomarker antibody for detection of neurodegenerative diseases and pathologies associated with tau protein, comprising:
   a light chain variable region having at least 85 percent of sequence identity to SEQ ID NO: 2 comprising an LCDR1 set forth in SEQ ID NO: 4, an LCDR2 set forth in SEQ ID NO: 6, and an LCDR3 set forth in SEQ ID NO:8; and
   a heavy chain variable region having at least 85 percent sequence identity to SEQ ID NO: 10 comprising an HCDR1 set forth in SEQ ID NO: 12, an HCDR2 set forth in SEQ ID NO: 14, and an HCDR3 set forth in SEQ ID NO:16,
wherein said antibody detects high molecular weight variants and a low molecular weight variants of tau protein, wherein the high molecular weight variants of tau protein are greater than 70 kDa and the low molecular weight variants of tau protein are less than 70 kDa.

2. A biomarker kit for detection and diagnosis of neurodegenerative diseases and tau protein-associated pathologies, comprising:
   i) chemical reagents for extracting blood proteins from blood samples;
   ii) chemical reagents for determining a concentration of the blood proteins present in the blood samples;
   iii) the antibody according to claim 1;
   iv) instructions for performing a test using the reagents i)-iii) and interpreting results of the test.

3. A biomarker antibody according to claim 1, wherein the biomarker antibody binds to the high molecular weight variants and the low molecular weight variants of tau protein in blood.

4. A pharmaceutical composition comprising, the biomarker antibody according to claim 1 and a pharmaceutically acceptable carrier.

5. A biomarker kit according to claim 1 wherein the biomarker antibody binds to the high molecular weight variants and the low molecular weight variants of tau protein in blood.

* * * * *

SEQUENCE LISTING

<160> NUMBER OF SEQ ID NOS: 16

<210> SEQ ID NO 1
<211> LENGTH: 337
<212> TYPE: DNA
<213> ORGANISM: Artificial sequence
<220> FEATURE:
<221> NAME/KEY: source
<223> OTHER INFORMATION: /note = "Description of artificial sequence:
      synthetic polynucleotide"

<400> SEQUENCE: 1

```
gacattgtga tgacacagtc tccatcctcc ctggctgtgt cagcaggaga gaaggtcact      60
atgacctgca aatccagtca gagtctgctc aacagtagaa cccgaaagaa ctacttggct     120
tggtaccagc agaaaccagg acagtctcct aaactgctga tctattgggc atccactagg     180
gaatctgggg tccctgatcg cttcacaggc agtggatctg ggacagattt cactctcacc     240
atcagcagtg tgcaggctga agacctggca gtttatttct gcaaacaatc ttataatctg     300
tacacgttcg gaggggggac caagctggaa ataaaac                              337
```

<210> SEQ ID NO 2
<211> LENGTH: 112
<212> TYPE: PRT
<213> ORGANISM: artificial sequence
<220> FEATURE:
<221> NAME/KEY: source
<223> OTHER INFORMATION: /note = "Description of artificial sequence:
      synthetic peptide"

<400> SEQUENCE: 2

Asp Ile Val Met Thr Gln Ser Pro Ser Ser Leu Ala Val Ser Ala Gly
1               5                   10                  15

```
              Glu Lys Val Thr Met Thr Cys Lys Ser Ser Gln Ser Leu Leu Asn Ser
                           20                  25                  30

Arg Thr Arg Lys Asn Tyr Leu Ala Trp Tyr Gln Gln Lys Pro Gly Gln
                       35                  40                  45

Ser Pro Lys Leu Leu Ile Tyr Trp Ala Ser Thr Arg Glu Ser Gly Val
               50                  55                  60

Pro Asp Arg Phe Thr Gly Ser Gly Ser Gly Thr Asp Phe Thr Leu Thr
               65                  70                  75                  80

Ile Ser Ser Val Gln Ala Glu Asp Leu Ala Val Tyr Phe Cys Lys Gln
                               85                  90                  95

Ser Tyr Asn Gly Tyr Thr Phe Gly Gly Gly Thr Lys Leu Glu Ile Lys
                              100                 105                 110

<210> SEQ ID NO 3
<211> LENGTH: 36
<212> TYPE: DNA
<213> ORGANISM: Artificial sequence
<220> FEATURE:
<221> NAME/KEY: source
<223> OTHER INFORMATION: /note = "Description of artificial sequence:
      synthetic peptide"

<400> SEQUENCE: 3
cagagtctgc tcaacagtag aacccgaaag aactac                                    36

<210> SEQ ID NO 4
<211> LENGTH: 12
<212> TYPE: PRT
<213> ORGANISM: Artificial sequence
<220> FEATURE:
<221> NAME/KEY: source
<223> OTHER INFORMATION: /note = "Description of artificial sequence:
      synthetic peptide"

<400> SEQUENCE: 4

Gln Ser Leu Leu Asn Ser Arg Thr Arg Lys Asn Tyr
1               5                   10

<210> SEQ ID NO 5
<211> LENGTH: 9
<212> TYPE: DNA
<213> ORGANISM: Artificial sequence
<220> FEATURE:
<221> NAME/KEY: source
<223> OTHER INFORMATION: /note = "Description of artificial sequence:
      synthetic peptide"

<400> SEQUENCE: 5 tgggcatcc                                                                   9

<210> SEQ ID NO 6
<211> LENGTH: 3
<212> TYPE: PRT
<213> ORGANISM: Artificial sequence
<220> FEATURE:
<221> NAME/KEY: source
<223> OTHER INFORMATION: /note = "Description of artificial sequence:
      synthetic peptide"

<400> SEQUENCE: 6

Trp Ala Ser
1

<210> SEQ ID NO 7
```

```
<211> LENGTH: 24
<212> TYPE: DNA
<213> ORGANISM: Artificial sequence
<220> FEATURE:
<221> NAME/KEY: source
<223> OTHER INFORMATION: /note = "Description of artificial sequence:
      synthetic peptide"

<400> SEQUENCE: 7
aaacaatctt ataatctgta cacg                                             24

<210> SEQ ID NO 8
<211> LENGTH: 8
<212> TYPE: PRT
<213> ORGANISM: Artificial sequence
<220> FEATURE:
<221> NAME/KEY: source
<223> OTHER INFORMATION: /note = "Description of artificial sequence:
      synthetic peptide"

<400> SEQUENCE: 8

Lys Gln Ser Tyr Asn Leu Tyr Thr
1               5

<210> SEQ ID NO 9
<211> LENGTH: 346
<212> TYPE: DNA
<213> ORGANISM: Artificial sequence
<220> FEATURE:
<221> NAME/KEY: source
<223> OTHER INFORMATION: /note = "Description of artificial sequence:
      synthetic polynucleotide"

<400> SEQUENCE: 9
caggtccaac tgcagcagtc aggggctgag cttgtgaagc ctggggcttc agtgaagatg      60
tcctgcaagg cttctggcta caccttcacc agctactgga tgcactgggt gaagcagagg     120
cctggacaag gccttgagtg gattggaaat gtttatcctg gtagtggtgg tactcactac     180
aatgagaagt tcaagagtaa ggccacactg actgtagaca atcctccag cacagcctac      240 atgcagctca gcagcctgac atctgaggac tctgcggtct attactgtgc aactctaact     300 gccctgact actggggcca aggcaccact ctcacagtct cctcag                    346

<210> SEQ ID NO 10
<211> LENGTH: 115
<212> TYPE: PRT
<213> ORGANISM: Artificial sequence
<220> FEATURE:
<221> NAME/KEY: source
<223> OTHER INFORMATION: /note = "Description of artificial sequence:
      synthetic peptide"

<400> SEQUENCE: 10

Gln Val Gln Leu Gln Gln Ser Gly Ala Glu Leu Val Lys Pro Gly Ala
1               5                   10                  15

Ser Val Lys Met Ser Cys Lys Ala Ser Gly Lys Thr Phe Thr Ser Tyr
            20                  25                  30

Trp Met His Trp Val Lys Gln Arg Pro Gly Gln Gly Leu Glu Trp Ile
        35                  40                  45

Gly Asn Val Tyr Pro Gly Ser Gly Gly Thr His Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
```

85                  90                  95

Ala Thr Leu Thr Ala Pro Asp Tyr Trp Gly Gln Gly Thr Thr Leu Thr
            100                 105                 110

Val Ser Ser
        115

<210> SEQ ID NO 11
<211> LENGTH: 24
<212> TYPE: DNA
<213> ORGANISM: Artificial sequence
<220> FEATURE:
<221> NAME/KEY: source
<223> OTHER INFORMATION: /note = "Description of artificial sequence:
      synthetic peptide"

<400> SEQUENCE: 11
ggctacacct tcaccagcta ctgg                                           24

<210> SEQ ID NO 12
<211> LENGTH: 8
<212> TYPE: PRT
<213> ORGANISM: Artificial sequence
<220> FEATURE:
<221> NAME/KEY: source
<223> OTHER INFORMATION: /note = "Description of artificial sequence:
      synthetic peptide "

<400> SEQUENCE: 12

Gly Tyr Thr Phe Thr Ser Tyr Trp
1               5

<210> SEQ ID NO 13
<211> LENGTH: 24
<212> TYPE: DNA
<213> ORGANISM: Artificial sequence
<220> FEATURE:
<221> NAME/KEY: source
<223> OTHER INFORMATION: /note = "Description of artificial sequence:
      synthetic peptide"

<400> SEQUENCE: 13
gtttatcctg gtagtggtgg tact                                           24

<210> SEQ ID NO 14
<211> LENGTH: 8
<212> TYPE: PRT
<213> ORGANISM: Artificial sequence
<220> FEATURE:
<221> NAME/KEY: source
<223> OTHER INFORMATION: /note = "Description of artificial sequence:
      synthetic peptide "

<400> SEQUENCE: 14

Val Tyr Pro Gly Ser Gly Gly Thr
1               5

<210> SEQ ID NO 15
<211> LENGTH: 24
<212> TYPE: DNA
<213> ORGANISM: Artificial sequence
<220> FEATURE:
<221> NAME/KEY: source
<223> OTHER INFORMATION: /note = "Description of artificial sequence:
      synthetic peptide"

<400> SEQUENCE: 15
gcaactctaa ctgcccctga ctac                                           24

```
<210> SEQ ID NO 16
<211> LENGTH: 8
<212> TYPE: PRT
<213> ORGANISM: Artificial sequence
<220> FEATURE:
<221> NAME/KEY: source
<223> OTHER INFORMATION: /note = "Description of artificial sequence:
      synthetic peptide"

<400> SEQUENCE: 16

Ala Thr Leu Thr Ala Pro Asp Tyr
1               5
```